(12) United States Patent
Unwin et al.

(10) Patent No.: US 8,580,104 B2
(45) Date of Patent: Nov. 12, 2013

(54) NANOTUBE ELECTROCHEMISTRY

(75) Inventors: Patrick Unwin, Coventry (GB); Julie Macpherson, Coventry (GB); Ioana Dumitrescu, Austin, TX (US); Jonathan P. Edgeworth, Austin, TX (US)

(73) Assignee: University of Warwick, Coventry (GB)

( * ) Notice: Subject to any disclaimer, the term of this patent is extended or adjusted under 35 U.S.C. 154(b) by 0 days.

(21) Appl. No.: 13/133,690

(22) PCT Filed: Dec. 11, 2009

(86) PCT No.: PCT/GB2009/002871
§ 371 (c)(1),
(2), (4) Date: Aug. 25, 2011

(87) PCT Pub. No.: WO2010/067083
PCT Pub. Date: Jun. 17, 2010

(65) Prior Publication Data
US 2011/0297556 A1 Dec. 8, 2011

(30) Foreign Application Priority Data

Dec. 12, 2008 (GB) .................................. 0822733.2

(51) Int. Cl.
*G01N 27/416* (2006.01)
*B05D 5/12* (2006.01)

(52) U.S. Cl.
USPC ..................... 205/792; 205/777.5; 205/794.5; 204/403.15; 977/957; 977/752; 977/750

(58) Field of Classification Search
USPC ............... 204/400, 403.01–403.15, 431, 280, 204/290.01, 290.15; 205/777.5, 789, 792, 205/794.5; 977/701, 712, 742–753, 977/920–922, 953, 957, 958
See application file for complete search history.

(56) References Cited

U.S. PATENT DOCUMENTS 6,916,614 B1 * 7/2005 Takenaka et al. ............ 435/6.11
2008/0280038 A1 11/2008 Ward et al.

FOREIGN PATENT DOCUMENTS

WO    WO2009016389 A1    2/2009

OTHER PUBLICATIONS

Wilson, NR, et al. "Assessment of the Electrochemical Behavior of Two-Dimensional Networks of Single-Walled Carbon Nanotubes" Analytical Chemistry, vol. 78, No. 19, Oct. 1, 2006, p. 7006-7015 & Supporting Information.*
Dumitrescu, I et al.: "Single-walled carbon nanotube network ultramicroelectrodes." Analytical Chemistry American Chemical Society US, May 15, 2008, vol. 80.
Bertoncello, Paolo et al.: "Trace level cyclic voltammetry facilitated by single-walled carbon nanotube network electrodes." Journal of the American Chemical Society, Sep. 12, 2007, vol. 129.

(Continued)

*Primary Examiner* — J. Christopher Ball
(74) *Attorney, Agent, or Firm* — Maginot, Moore & Beck, LLP

(57) ABSTRACT

An electrode for electrochemical analysis is described, the electrode comprising: an insulating surface; a three-dimensional network of carbon nanotubes situated on the insulating surface; and an electrically conducting material in electrical contact with the carbon nanotubes; wherein the carbon nanotubes are oriented substantially parallel to the insulating surface. Also described is a method of manufacturing the electrode, and a method of electrochemically analysing a solution using electrodes of this type, and an associated assay device or kit.

15 Claims, 8 Drawing Sheets

(56) References Cited

OTHER PUBLICATIONS

Edgeworth, Jonathan P. et al.: "Controlled growth and characterization of two-dimensional single-walled carbon-nanotube networks for electrical applications." Small, John Wiley and Sons, Weinheim Ander Bergstrasse, Germany, May 1, 2007, vol. 3.
McCreery, R.L., Chem. Rev. 2008, 108, 2646.
Saito, R. et al, Appl. Phys. Lett. 1992, 60, 2204.
Rosenblatt, S. et al., Nano Lett. 2002, 2, 869.
Gooding, J.J., Electrochim. Acta 2005, 50, 3049.
Britto, P.J. et al., Bioelectrochem. Bioenerg. 1996, 41, 121.
Luo, H.X., et al., Anal. Chem. 2001, 73, 915.
Moore, R.R., et al., Anal. Chem. 2004, 76, 2677.
Wang, J., Musameh, M., Anal. Chem. 2003, 75, 2075.
Valentini, F. et al., Anal. Chem. 2003, 75, 5413.
Liu, J. et al., Science 1998, 280, 1253.
Dumitrescu, I. et al., J. Phys. Chem. C 2007, 111, 12944.
Lawrence, Nathan S. R.P.D., Wang, Joseph, Electroanal.s 2005, 17, 65.
Duvall, S.H., McCreery, R.L., Anal. Chem. 1999, 71, 4594.
Li, J. et al., J. Phys. Chem. B 2002, 106, 9299.
Gabay, T. et al. Nanotechnology 2007, 035201.

* cited by examiner

Figures 1 a - d

Figures 3 a - d
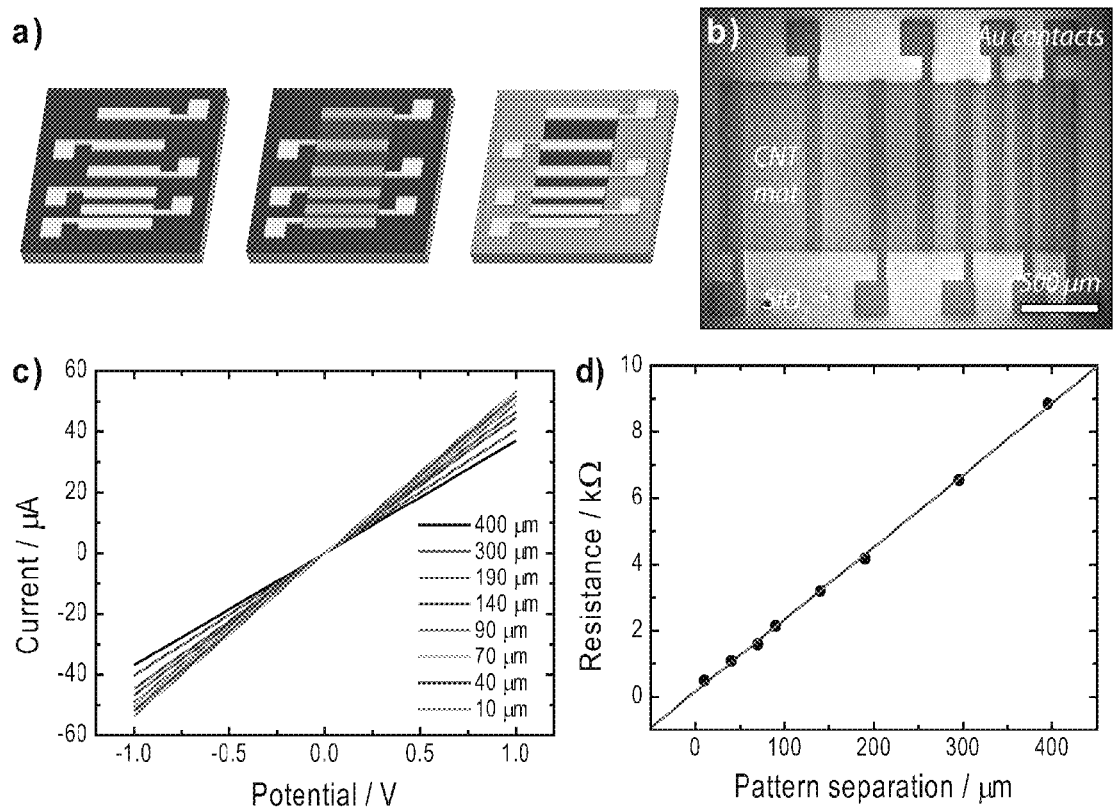

Figures 4 a - e
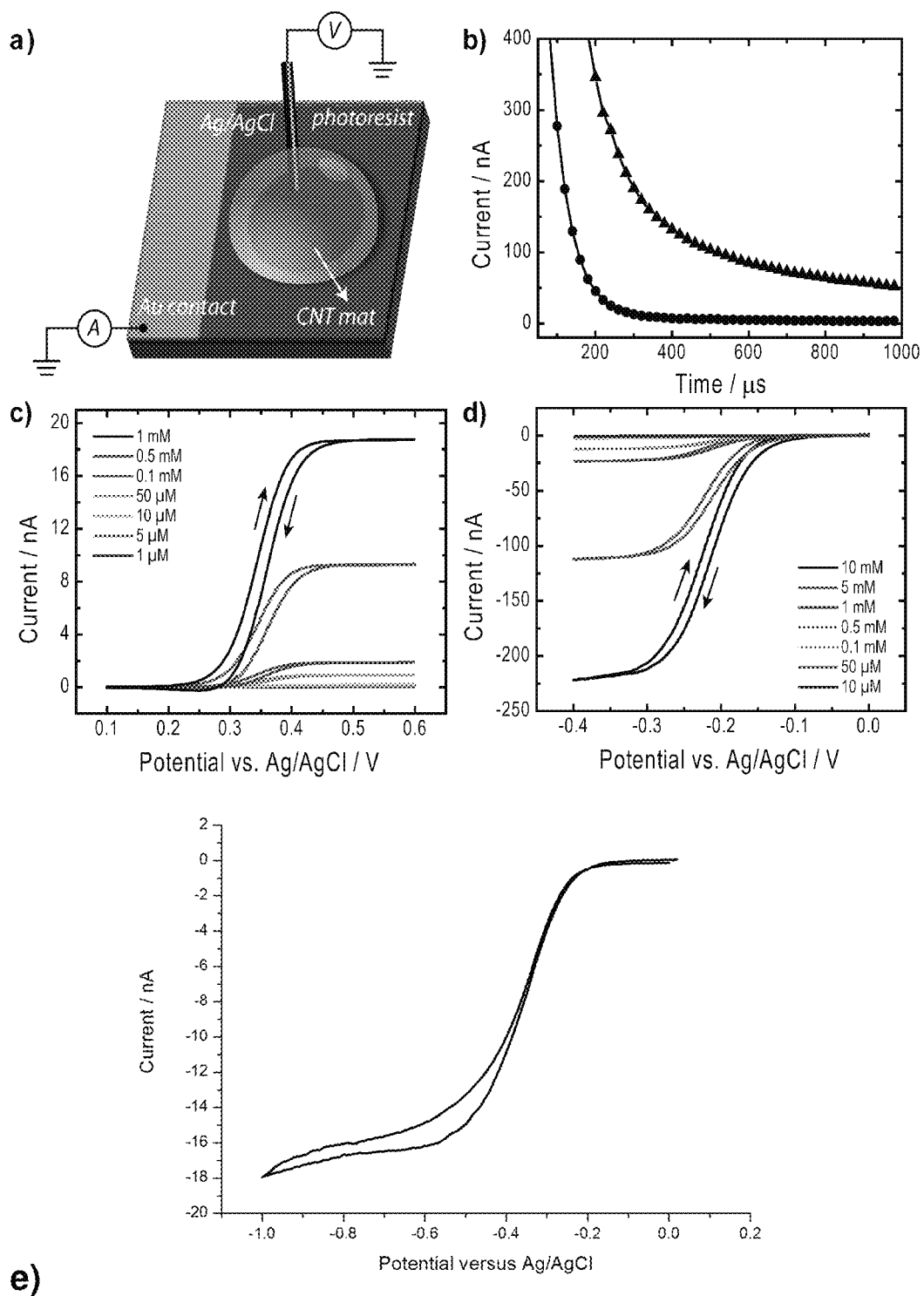

Figures 5 a - e
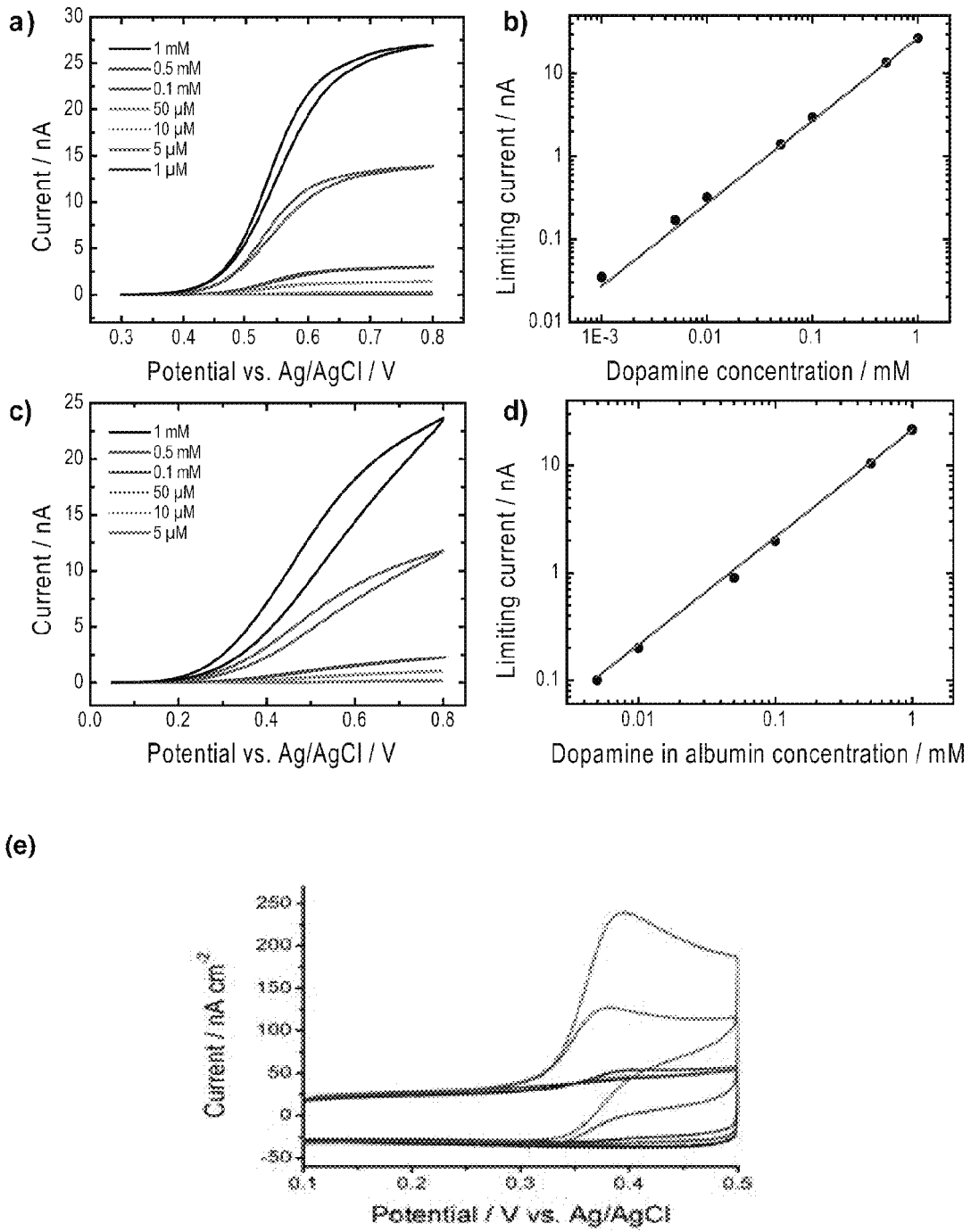

Figures 6 a – b
(a) (i) 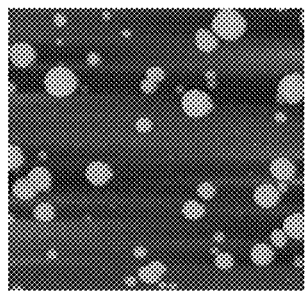 (ii) 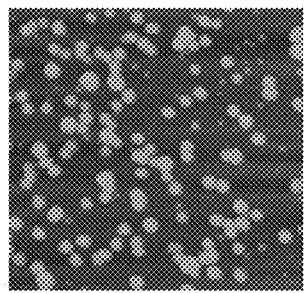 (iii) 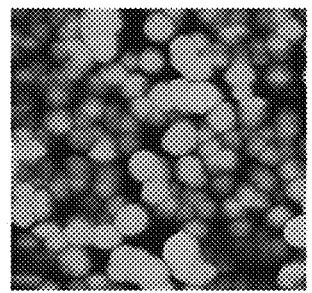
(b) (i) 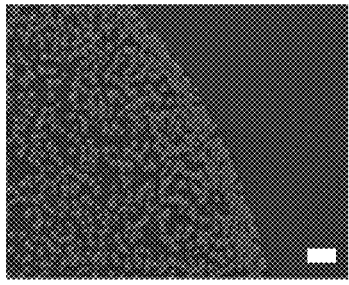 (ii) 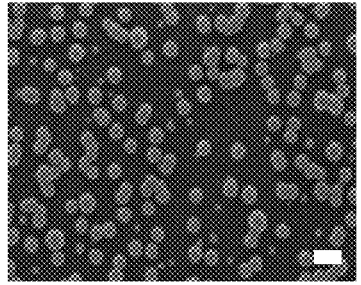 (iii) 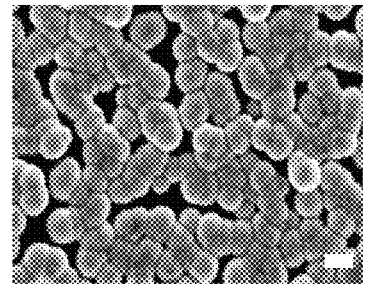

Figures 7(a) – (b)
(a)
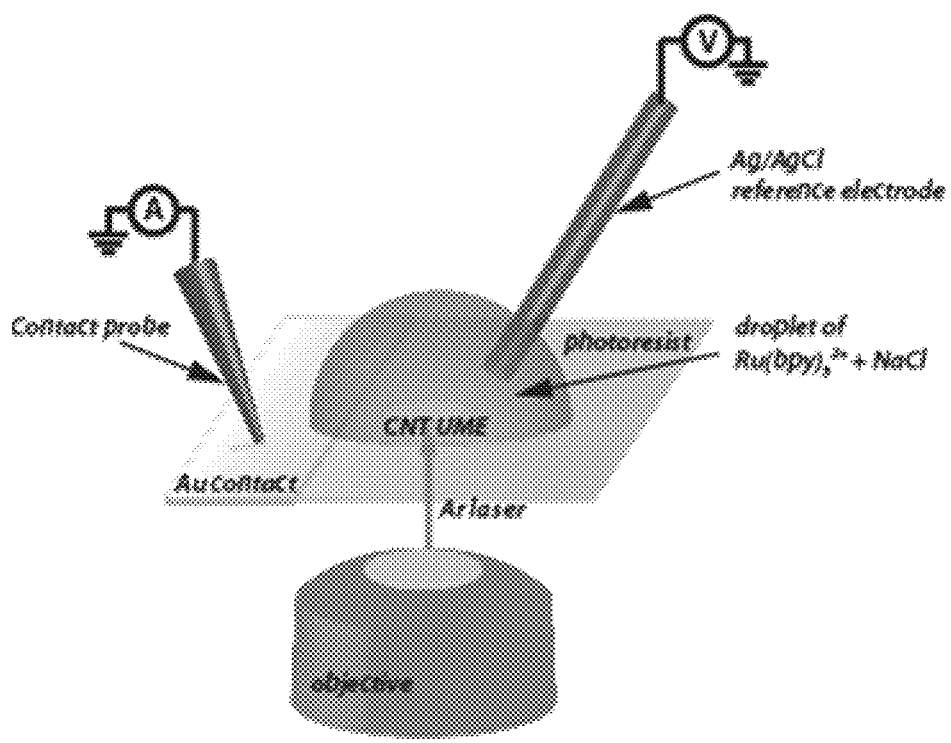
(b)
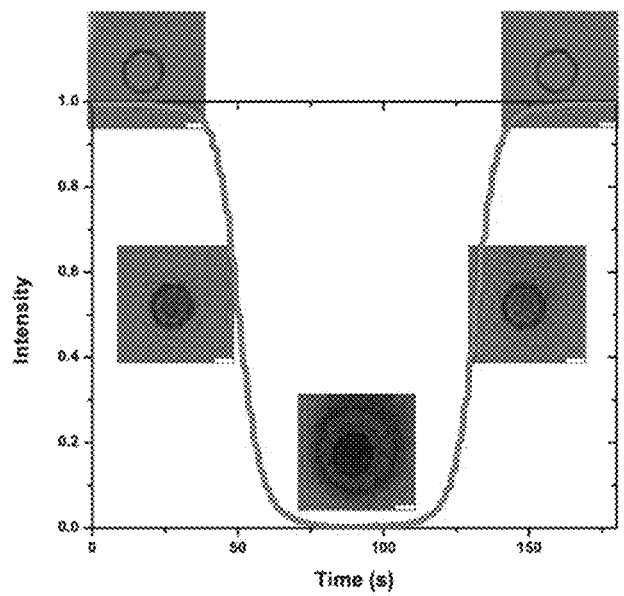

Figure 7(c) – (d)
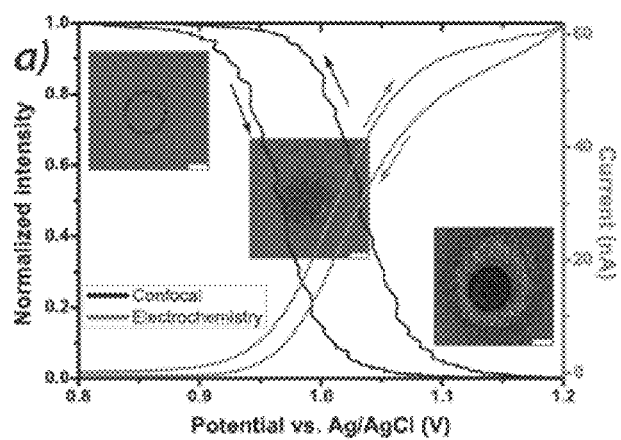
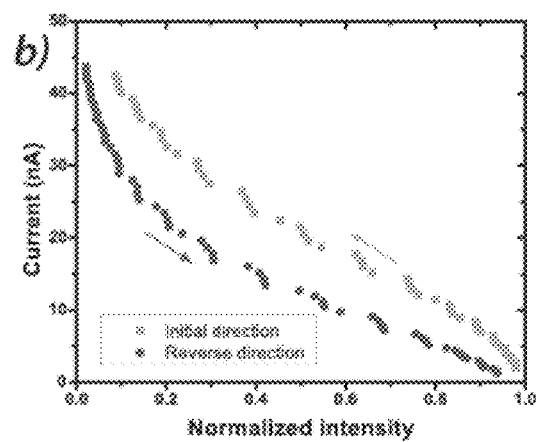

NANOTUBE ELECTROCHEMISTRY

PRIORITY

This application is a U.S. National Stage Application of International Patent Application PCT/GB2009/002871, titled Nanotube Electrochemistry, filed 11 Dec. 2009, which claims priority to Great Britain Application 0822733.2, filed 12 Dec. 2008, each incorporated herein by reference.

The invention relates to an electrode for use in electrochemical, particularly amperometric, analysis and/or detection. In particular, the invention relates to an electrode comprising a three-dimensional network of carbon nanotubes, and to a method for the electrochemical analysis and/or detection of compounds using the electrode.

Carbon materials are widely used in analytical electrochemistry due to their useful attributes notably their chemical stability, wide electrochemical potential window in aqueous solution and biocompatibility. The surface chemistry of carbon can promote electrochemical processes that are more difficult to observe on metal electrodes. Hence, carbon based electrodes are often superior to noble metals for the detection of organic and biological redox systems (R. L. McCreery, *Chem. Rev.* 2008, 108, 2646). Carbon nanotubes have very different structural and electronic properties to the classical carbon materials used in electrochemistry, e.g. glassy carbon, graphite and diamond (R. Saito et al. *Appl. Phys. Lett.* 1992, 60, 2204). The combination of high aspect ratio, good electrical conductivity and low capacitance makes carbon nanotubes excellent electrode materials (S. Rosenblatt et al., *Nano Lett.* 2002, 2, 869 and P. Bertoncello et al., *J. Am. Chem. Soc.* 2007, 129, 10982). Numerous studies have shown that carbon nanotube modified electrodes exhibit very attractive electrochemical properties, including reduced overpotentials, enhanced detection limits and increased sensitivity coupled with little or no surface fouling, in comparison to other carbon based materials, usually glassy carbon (P. Bertoncello et al., *J. Am. Chem. Soc.* 2007, 129, 10982; J. Wang, Electroanal. Chem., 2nd ed., Wiley, New York, 2000; J. J. Gooding, *Electrochim. Acta* 2005, 50, 3049; and I. Dumitrescu, et al., *Anal. Chem.* 2008, 80, 3598).

Traditionally, carbon nanotube electrodes are prepared essentially as composites, by randomly dispersing or confining the carbon nanotubes to an underlying support electrode (P. J. Britto, et al., *Bioelectrochem. Bioenerg.* 1996, 41, 121; H. X. Luo, et al., *Anal. Chem.* 2001, 73, 915; R. R. Moore, et al., *Anal. Chem.* 2004, 76, 2677; J. Wang, M. Musameh, *Anal. Chem.* 2003, 75, 2075; and F. Valentini et al, *Anal. Chem.* 2003, 75, 5413). For most of these applications, carbon nanotubes are first grown in bulk. Regardless of the carbon nanotube growth method, there is always a significant amount of impurities present. Purification pre-treatments, usually performed by boiling in a mixture of strong acids, shorten the carbon nanotubes and oxidatively damage the ends and sidewalls (J. Liu et al. *Science* 1998, 280, 1253), resulting in the introduction of electronic scattering centers with potentially damaging results to the performance of a carbon nanotube device (I. Dumitrescu et al, *J. Phys. Chem. C* 2007, 111, 12944). In addition, while pristine carbon nanotubes are known to have low intrinsic capacitance (S. Rosenblatt et al., *Nano Lett.* 2002, 2, 869), electrodes coated with processed carbon nanotubes can display remarkably high capacitance (R. P. D. Nathan S. Lawrence, Joseph Wang, *Electroanal.s* 2005, 17, 65). This has important implications for electrochemical sensor applications, where the best signal (from faradaic current) to background (mainly due to capacitive discharge) ratio is desired (A. J. Bard, L. R. Faulkner, *Electrochemical Methods Fundamentals and Applications*, Wiley, 2000).

The use of catalyzed chemical vapour deposition (cCVD) enables the growth of pristine carbon nanotubes on insulating surfaces, with no need for further purification. Under controlled growth conditions cCVD can result in the formation of multiply interconnected, random, two-dimensional (2D) networks of carbon nanotubes. Careful control of growth parameter enables control over the density of the network, which decides the network conductivity. Low-density networks demonstrate p-type semiconductor behavior, whilst high-density networks exhibit semi-metallic behavior (J. P. Edgeworth et al., *Small* 2007, 3, 860; US 2008/0280038). It has recently been shown that such "semi-metallic" carbon nanotube networks yielded a voltammetric response governed by the area of the support (rather than the area of the carbon nanotubes themselves) due to overlap of neighboring diffusion fields, in spite of a surface coverage of <1% (P. Bertoncello et al., *J. Am. Chem. Soc.* 2007, 129, 10982 and I. Dumitrescu et al., *Anal. Chem.* 2008, 80, 3598). The benefits of this are much improved discrimination against background signals, leading to unprecedented detection limits and fast response times. However, the resistivity of these networks is very much dependent on gate potential (varying from 77 k$\Omega$ square$^{-1}$ to 2.8 G$\Omega$ square$^{-1}$, depending on gate potential) leads to significant iR effects at higher analyte concentrations. For example, at a 100 µm diameter carbon nanotube network disk ultramicroelectrode (UME), cyclic voltammograms (CVs) become distorted at redox concentrations above 1 mM. In addition, the carbon nanotube networks perform poorly for the long time electrochemical detection of dopamine, which is known to adsorb to the electrode surface (S. H. DuVall, R. L. McCreery, *Anal. Chem.* 1999, 71, 4594). Deterioration of the current voltage response is observed after repeated cyclic voltammetric cycles, indicating blocking characteristics. At very low surface network coverage, even the blocking of few sites on the carbon nanotubes appears to have dramatic effects on the overall performance of the electrode. Thus, for many applications, higher density surfaces are required.

Carbon nanotube electrodes with a higher packing density have been prepared either by membrane filtration of carbon nanotube suspensions (J. Li et al., *J. Phys. Chem. B* 2002, 106, 9299) or by direct cCVD growth (T. Gabay, et al., *Nanotechnology* 2007, 035201). Meyyappan et al. prepared carbon nanotube paper electrodes by collecting the solid residue of acid refluxed carbon nanotubes. Direct cCVD synthesis of thick carbon nanotube mats on conducting tracks has also been reported. The carbon nanotube electrodes prepared in this way have thicknesses of 10-100 µm and significant inhomogeneities and impurities on the surface. The electrodes present very large volume specific capacitance, due to the post growth processing procedure and the three dimensional layered nature of the carbon nanotubes and are unsuitable for low concentration electrochemical detection.

It is, however, desirable to provide an electrode comprising carbon nanotubes which can be used for electrochemical detection across a wide range of solution concentrations (including low concentrations) and which is resistant to fouling. The invention seeks to address one or both of these problems. Further, the electrode of the invention comprises a three-dimensional network on an insulating surface to provide an electrode material with one or more features selected from: a low capacitance, low resistance, low background current and fast response times.

In accordance with a first aspect of the invention there is provided an electrode for electrochemical analysis comprising:

an insulating surface;

a three-dimensional network of carbon nanotubes situated on the insulating surface; and an electrically conducting material in electrical contact with the carbon nanotubes;

wherein the carbon nanotubes are oriented substantially parallel to the insulating surface.

As used herein the term "on" is intended to require at least partial direct contact between the elements/components described. Accordingly, where a first component is described as being "on" a second component, the presence of a complete, separating, layer of a third component between the first and second components is excluded.

As used herein the term "three-dimensional network" is intended to mean a tangled or meshed network of carbon nanotubes which are crosslinked, or otherwise contacted with other nanotubes in the same plane and/or adjacent planes of the network.

In many embodiments the carbon nanotube network covers more than 5% of the insulating surface. Often in the range 40-99.9%, generally 50-99.5%, in many embodiments at least 95% of the insulating surface, often at least 98%, at least 99% or at least 99.5% of the insulating surface. In some examples, the network provides substantially complete coverage of the insulating surface. Without being bound by theory, it is believed that this increase in total coverage enhances the stability of the carbon nanotube electrode in complex media, such as those found when studying biological systems. This improvement in stability provides the possibility of using these electrodes in biosensing applications.

It is often desirable that the network be of average thickness in the range 1 nm-200 nm, often 2 nm-150 nm, alternatively 4 nm-100 nm, in some examples 7 nm-50 nm, or 8 nm-20 nm. It can be preferred that the thickness of the network be in the range 8 nm-12 or 15 nm. Where the thickness of the carbon nanotube network is 15 nm or less the benefits of a substantially two-dimensional substrate are maintained, yet the thickness of the network is sufficient to substantially cover the insulating surface.

If the average diameter of a carbon nanotube is in the range 2-3 nm, it could be said that the three-dimensional network is from 1 to 100 nanotubes deep; often from 1 to 10 nanotubes; in some embodiments the network is 3, 4, 5 or 6 carbon nanotubes deep; however, the three-dimensional network of the invention is not formed from discrete layers but from a network of car bon nanotubes interlinked to form a porous mat. Whilst the nanotubes are aligned substantially parallel with the substrate, these may be tangled so that they are connected with other nanotubes in the same plane and adjacent planes of the network.

The surface coverage of any cross-sectional sample through the plane of the network parallel to the substrate will typically be no more than about 5.00, 4.00, 3.00, 2.50, 2.00, 1.75, 1.50, 1.25, 1.00, 0.75, 0.70, 0.65, 0.60, 0.55, 0.50, 0.45, 0.40, 0.35, 0.30, 0.25, 0.20, 0.15, 0.10, 0.05 or 0.01% of the insulating surface. It is the thickness of the network which provides the high level of overall coverage of the insulating surface, and forms the porous mat.

The density of the carbon nanotubes in any cross-sectional sample through the plane of the network parallel to the substrate is preferably at least about 1 $\mu m_{CNT} \mu m^{-2}$ (i.e. about 1 µm of nanotube per µm² of surface), more preferably at least about 2, 3, 4, 5, 6, 7, 8, 9 or 10 $\mu m_{CNT} \mu m^{-2}$.

The carbon nanotubes are preferably not localised over a small area of the electrode, but are distributed all over the electrode, as illustrated in e.g. FIGS. 1a and 1b.

The nanotubes are oriented substantially parallel to the insulating surface. It is generally desirable that each carbon nanotube is in contact with at least three other carbon nanotubes, particularly in the case of SWNT networks.

The statement "wherein the carbon nanotubes are oriented substantially parallel to the insulating surface" and equivalent statements are not intended to be absolute in the sense that there may be a trace presence of nanotubes either partially or entirely oriented other than parallel to the insulating surface, and that where these are present, such networks may also be in accordance with the invention. For instance, an electrode in which 0.01%, or 0.001%, or 0.0001% of carbon nanotubes are not substantially parallel may have physical properties substantially identical to those of an electrode where all of the carbon nanotubes lie in a plane parallel to the insulating surface and would therefore fall within the scope of the invention. Further, a low degree of orientation other than away from the plane of the substrate may be necessary in order for nanotubes within the three-dimensional network to contact nanotubes which are positioned closer to or further away from the substrate.

This contact between nanotubes maximises metallic conductance, this is because approximately one in every three SWNTs are metallic in nature, so this degree of interaction ensures that there is a consistent metal-metal contact across the network and hence conductance. More preferably, each SWNT is in contact with more than three others, such as 4, 5 or 6 others. However, on average, each SWNT is preferably in contact with at least three others.

In some examples the carbon nanotubes are randomly oriented. The random orientation will generally be within the plane of the network. This random orientation facilitates the formation of a network where each carbon nanotube is in contact with at least three other carbon nanotubes. It will generally not be the case that the carbon nanotube network contain secondary components other than carbon nanotubes, such as carbon fibres, graphite or other conductive components. Where the nanotubes are randomly oriented, they may be said to be tangled.

In other examples, the carbon nanotubes may be ordered within the network, where ordering is present the nanotubes may be said to form a mesh.

Unreacted nanoparticles may remain on the insulating substrate, and possibly within the three-dimensional network after growth of the carbon nanotubes.

The reacted nanoparticles are likely to be encapsulated within the nanotube framework, at one end of a nanotube, forming metal-carbide like structures (in the case of metal nanoparticles). At sufficient nanoparticle density, for certain cases, such as oxygen reduction, the electrochemical characteristics may advantageously be dominated by the metal nanoparticle-carbon nanotube composite structure.

In many examples the carbon nanotubes are single-walled carbon nanotubes (SWNTs); however multi-walled carbon nanotubes (MWNTs) may also be used. It is generally preferred that the carbon nanotubes are SWNTs.

The dimensions of the SWNTs in the network are usually about 5-10 µm in length and about 1-3 nm in diameter (although SWNTs may bundle together to form effective larger diameter structures). In the network the spacing between the carbon nanotubes on the electrode is dependent upon the density, which is controlled.

Electrical connection may be of any shape, in particular banded, rectangular, and circular. The electrical connection, is, generally made at one end of the insulating surface using an evaporated band of an electrically conductive material, although more than one point of electrical contact may be provided at different points on the insulating surface, such as by more than one evaporated or sputtered band of an electrically conductive material. It is also envisaged that one or more of the bands may be a ring, or arc of electrically conductive material encircling some or all of the carbon nanotube network.

The electrically conducting material may be any material as long as it is sufficiently conducting. Any conducting material which can be evaporated or sputtered may be used. Preferred examples of the electrically conducting material include Au, Pt, Pd, Ag, Ti or Cr (or a combination thereof). Most preferably, Au is used. To ensure good contact, it is preferable to put an adhesive (sticking) layer down first such as Ti or Cr prior to putting the conducting layer down. In this configuration there is no need to insulate the nanotubes.

At a sufficiently high density, and on typical voltammetric timescales, the network behaves predominantly like a thin metallic film. The sheet resistivity of such as film is <100 kΩ/square. To avoid problems such as ohmic drop contributing to the amperometric response small areas of the network are typically exposed to solution. This is most commonly achieved using photolithography; however, to avoid processing of the network a solution filled microcapillary electrochemical cell has also been employed. Importantly, for low concentration detection, the need to isolate only small areas of the network is no longer an issue as the current flowing will be small. In previous electrochemical studies with SWNT networks, small areas have been exposed to solution to minimize the effect of the network resistivity. Crucially, the low current density associated with low concentration detection, means that much larger network areas can be employed, thus simplifying the experimental arrangement significantly. For example, 1-50 µL drops can also be used on uninsulated networks.

In some embodiments, the nanotubes are pristine. In other, compatible, embodiments the nanotubes are functionalised. If they are functionalised, they are preferably functionalised with functional groups and moieties selected from polymers (e.g. ion-exchange polymers, conducting polymers or redox polymers), oxido-reductase enzymes (e.g. glucose oxidase, cholesterol oxidase, nicotinamide adenine dinucleotide) and dopants (e.g. ferrocene), generally known in the art. Alternatively, the nanotubes may be partially coated by metal deposition. Preferred metals for deposition include metals such as Pt, Au, Ag, Cu, Hg, Pd and semi-conducting materials such as Ti, TiN, CdSe, CdTe or CdS, and organic polymers e.g. P3HT (poly-3-hexylthiophene), pentacene, doped polyaniline etc. Some of these materials can be further functionalised with self assembled monolayers and dopants.

It is also possible to functionalise the insulating surface on which the nanotubes are located, but leaving the nanotubes unfunctionalised. The functionalised surface could act to generate species which can be detected at the pristine nanotubes. The functionalisation would be carried out after the growth and addition of the electrically conducting material (e.g. Au). The methods for grafting functional groups on to e.g. silicon oxide surfaces is well known in the art.

The insulating surface may be composed of any insulating material, the insulating material may be coated. The coating may be total or partial. In some embodiments the surface may comprise silicon, particularly a silicon oxide, e.g. a $Si/SiO_2$ containing surface (i.e. silicon with a silicon oxide coating), or quartz. In other embodiments, the surface may be coated with aluminium oxide, for instance, the surface may be a $Si/SiO_2$ surface which is at least partially coated with $Al_2O_3$. Alternatively, any insulating polymeric surface may be used, for instance, polyacetate, PDMS and/or PMMA may be used. This may be appropriate where the SWNT's have been transfer printed from the original growth surface onto the more flexible polymeric surface. Most preferably, a $Si/SiO_2$ containing surface is used.

Although the electrode is suitable for a wide variety of applications, in some examples the electrochemical analysis will be of bioelectrochemical systems. This is possible because of the combined lack of fouling of the electrode surface observed in use and the ability of the electrode to detect very low levels of analyte. The lack of fouling allows the electrodes to be used in a variety of media, including biological systems, whether in vivo or in vitro. The ability to detect low concentrations provides a sensor which can meaningfully detect analytes at the levels often found in biological samples.

The electrodes of the invention will often exhibit reversible electron transfer for iron and ruthenium redox reactions across a concentration range of the solution of 1 µM-10 mM. Indeed, electrochemical characterization of the carbon nanotube network UMEs revealed superb electrochemical properties, marked by reversible CVs recorded for iron and ruthenium complexes such as $FcTMA^+$ and $Ru(NH_3)_6^{3+}$, for a very wide concentration range, including low concentration detection (1 µM-10 mM). In spite of the very high surface coverage, the carbon nanotube network UMEs give incredibly fast response times and low background currents.

Further, the electrodes of the invention are, in many instances, stable to voltage sweeps in the range +1V to −1V and it has been found that when sweeping the bias voltage between −1 V and +1 V, that the carbon nanotube device behaved like a metallic film. The wide potential window is extremely useful for the analysis of low concentrations of chemical species having high oxidation and reduction formal potentials, such as dopamine.

In a further aspect of the invention there is provided a method of manufacturing an electrode according to the first aspect of the invention comprising:

depositing a quantity of catalytic nanoparticles onto an insulating surface;

exposing the insulating surface to heat, a source of hydrogen gas, and a source of a carbon-containing gas to grow the nanotubes; and depositing an electrically conducting material on the insulating surface so that it is in electrical contact with the carbon nanotubes.

One advantage of this method is that no annealing step needs to be carried out prior to the deposition of the catalytic nanoparticles; however, the inclusion of an annealing step is not excluded from the invention.

Preferably, the deposition of the electrically conducting material is carried out after the growth of the nanotubes. The carbon nanotubes of the invention are often grown using chemical vapour deposition, such as catalysed chemical vapour deposition (cCVD). This allows for the direct growth of pristine nanotubes. In some examples, each nanotube is generally grown from a single nanoparticle, in these examples the density of nanotubes is dependent upon the density of nanoparticles deposited onto the insulating surface. In the electrodes of the invention it will often be the case that unreacted nanoparticles remain on the surface after manufacture of the electrode.

After the step of growing the nanotube network on an insulating surface, it is also possible to transfer the network from the original insulating surface to another insulating surface, such as a polymer surface.

In the inventive method the catalytic nanoparticles may be metal nanoparticles, often transition metal nanoparticles, generally selected from the first row of the transition metal series. In many examples the catalytic nanoparticles will be cobalt, nickel or iron, although cobalt has been found to work most effectively either alone or in combination with other metals. Other metals may be used. Combinations of the metals may be used. Insulating particles such as diamond or silicon dioxide may also be used.

Additionally, when an iron-based catalyst is used, the iron may be provided in the form of ferritin, rather than from an e-beam of evaporated iron atoms (as ferritin is significantly cheaper and access to very sophisticated electron beam lithography is not required), as well as different oxidation and growth (reduction) conditions.

The nanoparticles may be deposited using a variety of methods known to the person skilled in the art. The nanoparticles may be formed from metal deposited onto the insulating surface. This may be in sub-monolayer amounts, or a layer of metal (which may be a monolayer, bi layer, trilayer or multiply layered). In some examples, the metal is melted (often by annealing) either prior to or during the growth of the carbon nanotubes to allow the formation of nanoparticles on the surface.

The carbon-containing gas may be any carbon containing gas, such as a short chain alkane, alkene, ether (such as diethyl ether), carbon monoxide or alcohol. Where the carbon-containing gas is a short chain alkane, it may be a $C_1$-$C_5$ alkane, for instance methane, ethane or propane. Where the carbon-containing gas is an alkene, it may be a $C_1$-$C_5$ alkene, such as ethene, propene or butene. Where the carbon-containing gas is an alcohol it will generally be a $C_1$-$C_5$ alcohol; often methanol, ethanol or propanol. The most commonly used carbon-containing gas is ethanol.

It is preferred that the carbon-containing gas be introduced to the catalytic nanoparticles in a carrier, often the carrier will be an inert gas, although hydrogen may be used. The use of an inert gas reduces the flammability of the system, improving safety. The inert gas may be selected from a noble gas (e.g. helium, neon, argon, xenon), nitrogen, or combinations thereof. Often the inert gas will be a noble gas, most preferably argon.

It is generally preferred that the carbon nanotube network be formed directly on thermally oxidized silicon substrates using cCVD process. cCVD processes convert the carbon source into highly crystalline nanotubes, at high temperatures and in the presence of a catalyst. In one embodiment a thin layer of cobalt is used as the catalyst and ethanol vapour as the carbon source. In these embodiments it is preferred that argon is present as a carrier for ethanol. The amount of cobalt, the flow rate of hydrogen and of ethanol vapour, and temperature can be optimized for the production of high-quality carbon nanotube network with the properties of the invention.

Ultramicroelectrodes of any geometry, although discs are preferred, can be formed in accordance with the method detailed above if a layer of resist is then added and a confocal laser or mark aligner used to remove some of the resist in a defined area.

A further aspect of the invention relates to a method of electrochemically analysing a solution, comprising:

providing an electrode with an insulating surface having a three-dimensional network of carbon nanotubes situated thereon; wherein the carbon nanotubes are oriented substantially parallel to the insulating surface;

bringing a sample of the solution into contact with the carbon nanotubes; and applying a potential across the electrode to electrochemically analyse the sample;

wherein the solution has a concentration in the range 1 nM-100 mM.

This method has the advantage that a cleaning or pretreatment procedure is not always needed prior to use of the analysis and as the electrode is highly resistant to fouling, even with traditionally challenging solutions such as protein containing solutions of dopamine. However, where appropriate a polymer layer may be added to prevent competitive reactions occurring at the nanotube surface.

The use of these electrodes (single or multiple) for in-vitro and in-vivo electrochemical measurements in biological tissues, includes measurements where the nanotube network electrode (pristine or functionalized) is held close to the region of interest and/or in direct contact with it.

A wide range different electrochemically active species may be analysed using the method of the invention and a wide range of solvents may be used. These include organic solvents, and aqueous systems. The aqueous systems may be samples from biological systems (natural biological solutions), or synthetic mimics of biological systems (synthetic biological solutions). The biological solutions may include blood, plasma, urine, saliva, semen, amniotic fluid, bile, lymph, and combinations thereof.

Often the electrochemical species to be analysed will be a species commonly found in biological systems, such as neurotransmitters (including the catecholamines), hormones and vitamins. Such compounds would include dopamine, serotonin, nor adrenaline, adrenaline, glutamate, GABA, Vitamin E, B12 or B6. Toxins, medicaments and other substances ingested may also be observed.

To demonstrate the power of the electrode, disk-shaped UME's were fabricated using the carbon nanotube network. The UME's were tested using a biologically challenging molecule under conditions that mimic in-vivo environment, where typically the electrode would be expected to foul. It was found that the electrode can be used successfully for the electrochemical detection of the neurotransmitter dopamine at concentrations in the µM range (in the presence of albumin, an in-vivo mimic), with no surface fouling even after extensive use. The enhanced electrochemical properties of the carbon nanotube network, the simple micro-fabrication preparation procedure as well as their biocompatibility and durability make the cCVD grown carbon nanotube network are of use for bioelectrochemical applications.

Further, the nanotubes could be functionalized with e.g. enzymes such as glucose oxidase, cholesterol oxidase or nicotinamide adenine dinucleotide, including the use of polymers to aid the functionalisation, and could be used in, for instance, the analysis and/or detection of sugars such as glucose, or of other substances.

The carbon nanotubes of the invention may be used in the electrochemical analysis of solutions having concentrations in the range 1 nM-1M, often 500 nM-100 mM, preferably 1 µM-10 mM, in some embodiments 5 µM-5 mM. The ability to detect electrochemical species across such a wide range of concentrations is rare in carbon nanotube electrode 2D networks as such systems often exhibit significant iR effects at higher concentrations of analyte.

The electrode may be used in amperometric gas sensing, wherein the nanotube network electrode (pristine or functionalised as described herein) functions as a working electrode in a cell comprising an electrolyte (solution or polymer), designed in such a way to allow the ingress of an analyte gas, which is detected amperometrically.

The surface coverage of any cross-sectional sample through the plane of the network parallel to the substrate is preferably of the order of 0.1%, although it is preferred that the total coverage provided by the network be at least 99% of the insulating surface, often the network will provide substantially complete coverage of the insulating surface.

When analysing a solution according to the invention, the solution is preferably brought into contact with the nanotubes by adding a droplet of it onto them. A potential is then applied between a working electrode in electrical contact with the electrically conducting material and a reference electrode (such as Ag/AgCl) which is positioned within the droplet. Droplets of the solution to be analysed are placed on the nanotubes on the insulating surface and create a relatively large planar diffusion area over the controlled density of nanotubes.

The electrode of the invention could also be extended to use in microelectrodes (i.e. (electrodes where the characteristic dimension is 100 µm or lower) and microelectrode arrays, using lithography to define the electrode area. Such microelectrodes (or ultramicroelectrodes—UMEs) present interesting attributes over conventional electrodes. Advantages include high mass transfer rates, short response times, low ohmic drop and reduced double layer charging. Traditionally, UMEs are made by sealing a fine wire in an insulator, by electrophoretic coating or using microlithographic techniques. Due to their useful properties, UMEs have found a wide range of applications in the fields of electroanalysis, sensors and scanning electrochemical microscopy.

The electrode of the invention could also be extended to flow systems and other detection methods, such as pulsed voltammetric methods and hydrodynamic modulation techniques, in addition to the droplet analysis. It can also serve as a platform on which modified layers could be added, such as polymers (e.g. ion exchange, redox), metal and semi-conducting nanoparticles. By moving to these new formats, the possibility for fast scan CV analysis and short time chronoamperometry is also realized.

The electrode of the invention could also be used as a transparent electrode in photoelectrochemical studies, or spectro-electrochemical analysis, whereby light passing through the electrode, or totally-internally reflected at the electrode/solution(analyte) interface, is used to analyse and/or photoexcite chemicals in solution for subsequent electrochemical detection or to analyse the products/intermediates of electrochemical reactions.

Transparent electrodes using the electrode of the invention and use of electrodes of the invention in photoelectrochemical structures, and/or spectro-chemical analysis is also covered by the invention.

The invention therefore also envisages an assay device or kit which comprises an carbon nanotube-based electrode as described above. The assay device or kit may also further comprise a counter electrode, a reference electrode and optionally a flow cell, as well as preferably a recordal means for the obtaining of data. The reference electrode may be protected with a thin polymer film to enhance its stability.

Unless otherwise stated each of the integers described in the invention may be used in combination with any other integer as would be understood by the person skilled in the art. Further, although all aspects of the invention preferably "comprise" the features described in relation to that aspect, it is specifically envisaged that they may "consist" or "consist essentially" of those features outlined in the claims.

The present invention will now be explained in more detail with reference to the accompanying Figures.

FIG. 3a is a schematic of the lithographic procedure for fabricating the devices used in the resistivity measurements;

FIG. 3b is a FE-SEM image of the two terminal devices used for resistivity measurements;

FIG. 3c is a graph illustrating the current-voltage characteristics for various pattern separations when sweeping the bias voltage between −1 V and +1 V, resistance values for each pattern separation are calculated from the slope of the straight line;

FIG. 3d is a plot of resistance versus pattern separation used to calculate $R_c$ and $\rho_s$;

FIG. 4a is a schematic of the 100 µm carbon nanotube network TIME and the experimental droplet cell set-up used for electrochemical measurements;

FIG. 4b is a series of current-time discharge curves at a 100 µm diameter carbon nanotube network UME (●) and 100 µm Pt UME (▲) sealed in glass;

FIG. 4c is a cyclic voltammogram of FcTMA$^+$ oxidation at different concentrations in 0.1 M NaCl supporting electrolyte at a 100 µm diameter carbon nanotube disk UME, scan rate in all cases was 4 mV s$^{-1}$;

FIG. 4d is a cyclic voltammogram of Ru(NH$_3$)$_6^{3+}$ reduction at different concentrations 0.1 M NaCl supporting electrolyte at a 100 µm diameter carbon nanotube disk UME. Scan rate in all cases was 4 mV s$^{-1}$;

FIG. 4e is a cyclic voltammogram of oxygen reduction in a solution containing 8 µM fluorescein in 0.1 M KCl solution at a 50 µm diameter carbon nanotube disk UME. Scan rate was 10 mV s$^{-1}$.

FIG. 5a is a cyclic voltammogram of dopamine at different concentrations in PBS;

FIG. 5b is a plot of limiting currents vs. mediator concentration and linear fits (solid lines) for dopamine in PBS;

FIG. 5c is a cyclic voltammogram of dopamine at different concentrations in 4% (w/w) albumin in water; and FIG. 5d is a plot of limiting currents vs. mediator concentration and linear fits (solid lines) for dopamine in 4% (w/w) albumin in water.

Figure 1:
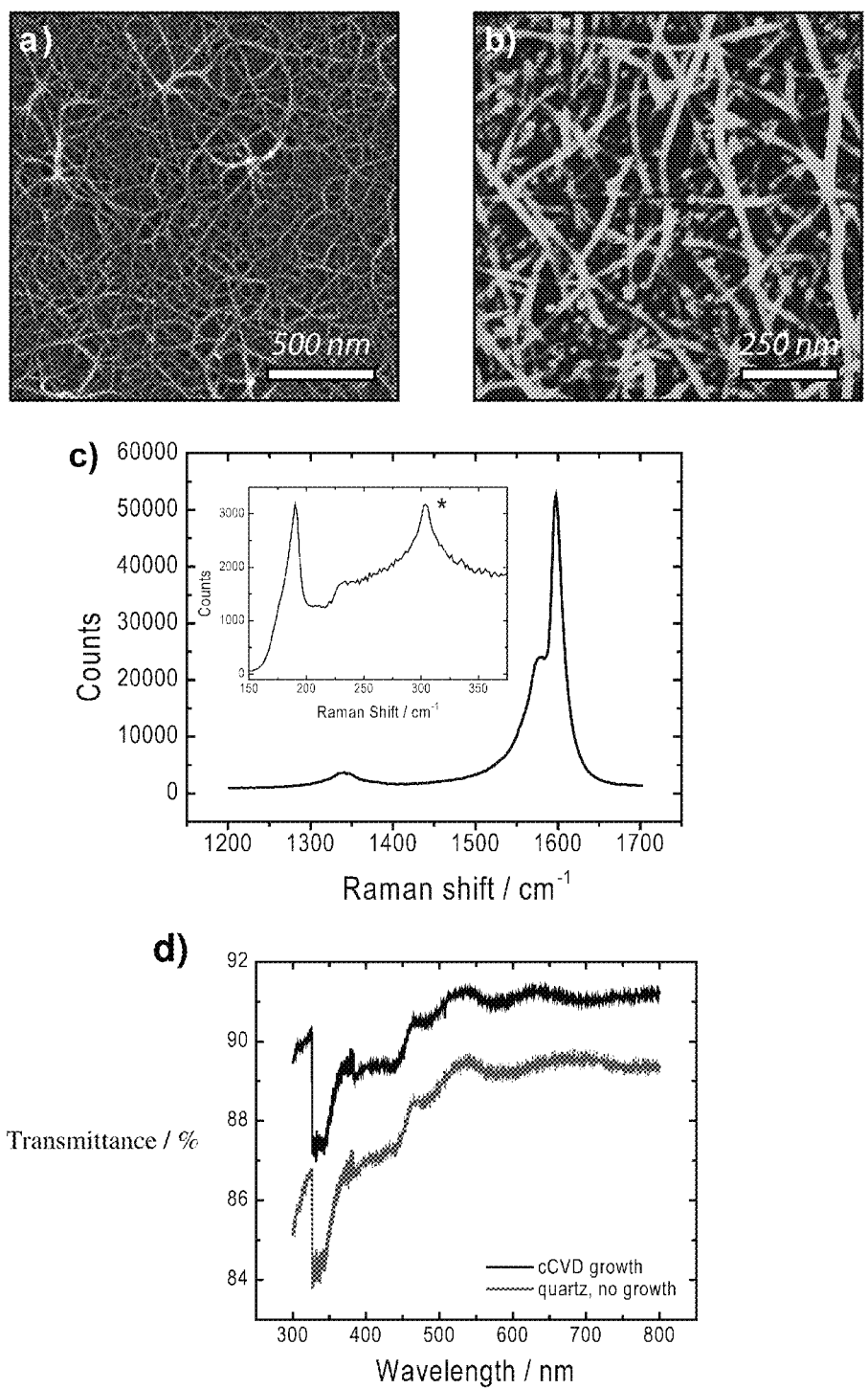
FIG. 1a is a field emission scanning electron microscopy (FE-SEM) image of a carbon nanotube network grown from cobalt nanoparticles.
FIG. 1b is an atomic force microscopy (AFM) image of the network of FIG. 1a, full height scale is 10 nm.
FIG. 1c is a micro-Raman spectrum of the network sample covering the 1300-1700 cm$^{-1}$ region, the inset shows the low frequency range and the peak marked with * belongs to the silicon substrate. A 514 nm (2.41 eV) argon laser with a spot size of 2.5 µm was used.
FIG. 1d is a wavelength-transmittance curve of the percentage light transmitted through quartz after carbon nanotube network growth (topline cCVD, lower line quartz)

FIG. 5e is a cyclic voltammogram of serotonin detection at different concentrations FIG. 6 shows AFM (5 µm×5 µm) and FE-SEM images of Pt NPs deposited onto high density SWNT networks after different numbers of CV cycles have been run on the electrode in a Pt plating solution; (a,b: i) 1 cycles (a,b: ii) 5 cycles and (a,b iii) 10 cycles. The z full height scale of AFM images is 400 nm, whilst for the FE-SEM images it is 400 nm in (biand ii) and 2 µm in (biii).

FIG. 7 (a) is a schematic of one possible use of a SWNT network electrode as a transparent electrode. Here, the electrode is on a slide on top of an inverted scanning laser confocal microscope. The electrode is poised at a potential where electrolysis of a redox couple present in solution causes the local fluorescence intensity to change which is mapped by the confocal microscope as shown in FIGS. 7 (b)-(d).

The invention will also be further explained in the following Examples, which are intended to be merely illustrative and are in no way intended to limit the scope of the invention.

Preparation of SWNT Networks

Growth of SWNT networks by cCVD was carried out by placing highly doped Si substrates of about 1 cm square, in a 1 inch (2.54 cm) tube furnace, after deposition of cobalt by spluttering. Under a flow of $H_2$, the furnace was heated from room temperature to 850° C. in 10 minutes, and then from 850° C. to the growth temperature in a further 10 minutes. The furnace was held at this temperature for 5 minutes, and ethanol was then introduced in argon for a set period of time, this being the growth time. After growth, the substrate was allowed to cool in the furnace under a flow of $H_2$ only. Once the temperature had reached less than 200° C. the sample was removed. A complete growth cycle takes about 1 h, and up to 8 samples can be grown at any one time (limited by the temperature uniformity in the tube furnace used).

To control the positioning of the SWNTs in a network in particular regions on a substrate surface, this can be carried out either before or after SWNT growth, referred to as pre-growth patterning and post-growth patterning respectively. Pre-growth patterning involves restricting the SWNT network growth to certain areas by selective placement of the metal catalyst. This can be done using for example photolithography, electron beam lithography, 'soft' lithography or shadow masking.

Post-growth patterning involves selective removal of the SWNT network after growth by an etchant such as a $CO_2$ snow jet treatment, or a plasma treatment. Photolithography was used to pattern photoresist on a SWNT network sample, protecting the SWNT network except for in the desired regions. An oxygen plasma treatment (100 W for 1 minute at $6\times10^{-1}$ mbar in an Emitech K1050X Plasma Asher) was then used to remove the exposed SWNTs and the photoresist removed. The oxygen plasma completely removes the nanotubes that were exposed to the oxygen plasma, leaving sharply cut ends. The effective resolution of post-growth patterning is given by the average spacing between the nanotubes within the network; as a result it can easily be achieved to sub-micron accuracy and in any pattern that can be lithographically defined.

Materials

Insulating Surface: Silicon/silicon dioxide from IDB Technologies Ltd, n-type silicon, 525 mm thick with a 300 nm thermally grown silicon dioxide layer.

Solutions: All chemicals were used as received. Aqueous solutions were prepared using Milli-Q reagent water (Millipore Corp.). Solutions for cyclic voltammetry consisted of hexaamineruthenium (III), $Ru(NH_3)_6^{3+}$, chloride (99%, Strem), (ferrocenylmethyl)trimethylammonium, $FcTMA^+$, hexafluorophosphate and dopamine (Sigma Chemicals). $FcTMA^+$ hexafluorophosphate was prepared via the metathesis of the corresponding iodide salt (99%, Strem) with ammonium hexafluorophosphate (99.5%, Strem).

Background electrolyte solutions consisted of NaCl (99+ %, Sigma-Aldrich), phosphate buffer saline (Fluka) and albumin.

Procedures

Cyclic voltammetry and chronoamperometry experiments employed a two electrode droplet cell set-up. Electrical connection to the gold electrodes was made with a sharp tip probe (xyz 300TR Quarter Research). A drop of electrolyte solution (~30 μL) containing the species of interest was placed over the exposed carbon nanotube area and a chlorinated silver wire, Ag/AgCl reference electrode, was positioned inside the drop. Current-voltage curves were recorded using a DAQ card (DT9800, Data Translations) for both analog output and input, controlled by purpose-written LabVIEW software, and coupled to a homebuilt current follower. Current-time measurements were acquired using a home-made triangular wave-pulse generator, current follower, and a NIC310 (Nicolet) digital storage oscilloscope. Within the experimental timescales employed, solution evaporation was not problematic, i.e. there was no noticeable change in the steady-state UME current for diffusion-controlled electrolysis of the mediator in bulk solution during the course of the various experiments. All measurements were made at a temperature of 22±1° C.

EXAMPLES

Example 1

Characterisation of the Carbon Nanotube Networks

FIG. 1 shows the characterization of a typical cCVD growth sample. The field emission scanning electron microscopy (FE-SEM) image in FIG. 1a) shows a carbon nanotube network, with multiply interconnected, randomly oriented carbon nanotubes, lying parallel to the substrate. Although any cross-section through the three-dimensional network is of relatively low surface coverage, a near complete surface coverage from the network as a whole arises as a result of several nanotubes overlapping at different distances within the network from the substrate. Without being bound by theory, it is believed that the three-dimensional network is formed from nanotubes, some of which initially grow upwards away from the substrate surface (although some may align on the surface) and then realign during growth (perhaps under their own weight) to form a three-dimensional network of nanotubes resting upon one another and which are interlinked/connected but oriented substantially parallel to the substrate.

The atomic force microscopy (AFM) image in FIG. 1b), reveals occasional small pore openings within the carbon nanotube network. The AFM surface profile analysis gives a height difference of 10 nm between the substrate and the maximum carbon nanotube network thickness, corresponding to the presence of a network which is a maximum of 4-6 carbon nanotubes deep. This is further established by cCVD growth on transparent quartz substrates which exhibit no change in percentage transmitted light after the carbon nanotube network growth (FIG. 1d).

FIG. 1c) shows the micro-Raman spectrum of a carbon nanotube network sample covering the 1300-1700 $cm^{-1}$ region where both the tangential modes derived from the in-plane Raman vibrations in graphite (G-band, 1500-1600 $cm^{-1}$), and the disorder modes (D-band in the region 1300-1400 $cm^{-1}$) are seen. The shape and position of the G-band positively identifies the sample to contain single-walled carbon nanotubes (SWNTs) and the very small D-band indicates they are of high quality. The low frequency vibrations (radial breathing mode) in FIG. 1c) inset also support the presence of SWNTs. However, AFM analysis also shows the presence of larger diameter carbon nanotubes (5-7 nm), possibly indicating that they are either small multi-walled carbon nanotubes (MWNTs) or bundles of several SWNTs.

Figure 2:
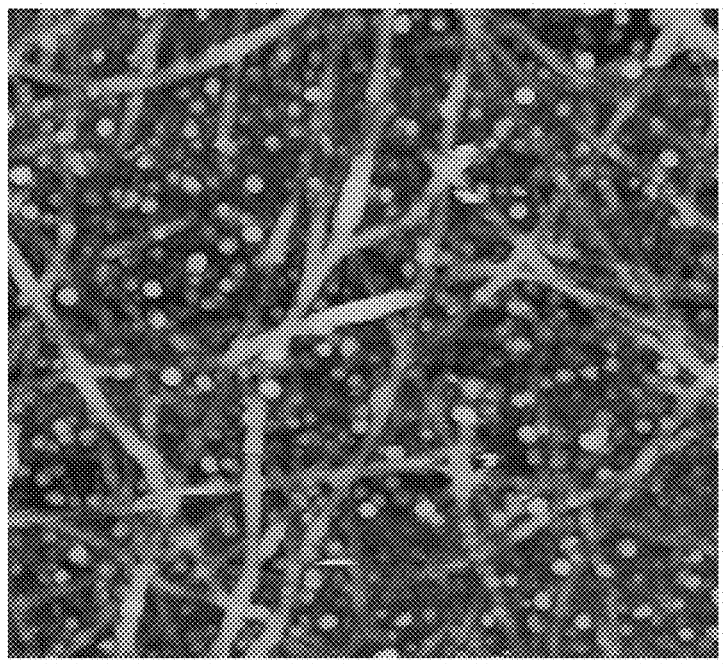
FIG. 2 is an atomic force microscopy (AFM) image of a carbon nanotube network; grown from cobalt nanoparticles at 850° C.

FIG. 2 is an atomic force microscopy (AFM) image of a carbon nanotube network; grown from cobalt nanoparticles on a cobalt deposition time of 10 seconds. The growth temperature was 850° C., and growth time was 10 minutes. The hydrogen flow rate was 150 sccm, and the Argon-ethanol flow rate 850 sccm. The network produced under these conditions is less dense than the network shown in FIG. 1, the image shows unreacted nanoparticles and a network of density in the region of 50% coverage.

Example 2

Conductivity of the Carbon Nanotube Networks

The use of the carbon nanotube networks in electrochemical applications relies on their electrical properties. In order to characterize the conductivity of the networks, devices were fabricated using a three-step process, as shown in FIG. 3a): 1) The carbon nanotube networks were grown as described above and a pattern of electrodes with varying separations was defined by photolithography; 2) the carbon nanotubes between the electrodes were protected by a photoresist layer; 3) the carbon nanotubes not between the electrodes were removed by an oxygen plasma treatment.

FIG. 3b) shows an FE-SEM image of a fabricated device. Current-voltage (i-V) characteristics were obtained for different electrode separations, FIG. 3c), when sweeping the bias voltage between −1 V and +1 V. It was found that the carbon nanotube device behaved like a metallic film, showing linear i-V response for the chosen bias voltage range. The resistance of this two-terminal device is given by:

$$R = s\frac{\rho_s}{l} + R_c \quad (1)$$

where s is the separation of the electrodes, l their length, $R_c$ the contact resistance between the metal electrodes and the carbon nanotube network and $\rho_s$ the 2D sheet resistivity. Resistance values for individual electrode separations were calculated from the slope of i-R plots. From the straight-line fit in FIG. 3d), a contact resistance of 165Ω and a sheet resistivity of 20 kΩ square$^{-1}$ can be extracted.

Example 3

Stability of the Electrode

For electrochemical validation, 100 μm diameter carbon nanotube network UMEs were fabricated using lithography (I. Dumitrescu et al., *Anal. Chem.* 2008, 80, 3598). A schematic of the device used is given in FIG. 4a). A major concern when considering the electrochemical performance of the carbon nanotube network UMEs is traces of catalyst nanoparticles (such as cobalt, or which ever metal is used). Accordingly, background electrolyte CV experiments were carried out in 0.1 M NaCl and 0.1 M $HNO_3$ and revealed no cobalt stripping peaks, even after extensive scanning. As a control experiment, cobalt was electrodeposited onto the carbon nanotube network from a $CoCl_3$ solution and CVs taken in 0.1 M NaCl showed signature cobalt stripping peaks in the region 0 to 0.8 V (vs. Ag/AgCl). This effect can be understood considering the fact that cobalt is either encapsulated within the carbon nanotube frame or is rendered inactive (possibly as a carbide) by the cCVD growth treatment. However it is also interesting to note that if the density of catalystic Co nanoparticles on the surface is significantly increased (e.g. ≥20 s Co sputter time, 1 kV 10 mA) then it is possible to observe interesting voltammetric signatures, for example this material becomes very catalytically active towards the reduction of oxygen (FIG. 4e). Importantly, the wide potential window and the small background currents are extremely useful properties for the analysis of low concentrations of chemical species having high oxidation and reduction formal potentials, such as dopamine.

The time response of the carbon nanotube network UME was investigated using chronoamperometry. The current-time response of a typical SWNT network UME (●) is given in FIG. 4b). Also shown is the response of a 100 μm diameter Pt disk UMEs (▲) sealed in glass. The potential of the UMEs was stepped from 0.0 V to 0.2 V vs. Ag/AgCl, in a solution containing 0.1 M NaCl. At 0.2 V no faradaic process occurs at the UMEs. The charging current, i, decreases exponentially in time, t, at a rate dictated by RC, the cell time constant, as shown in FIG. 4b). However, the exponential decay of the charging current is significantly faster for the 100 μm carbon nanotube network UME, when compared with the 100 μm Pt UME. This is very surprising for a material of near complete surface coverage and is explained by the very low intrinsic capacitance that has been observed for pristine carbon nanotubes (S. Rosenblatt, et al., *Nano Lett.* 2002, 2, 869 and P. Bertoncello et al., *J. Am. Chem. Soc.* 2007, 129, 10982).

Further electrochemical characterization of carbon nanotube network UMEs was undertaken by studying their CV response to two simple one electron, outer-sphere redox species. FIGS. 4c) and 4d) show typical CVs for the oxidation of FcTMA$^{+/2+}$ (concentration range 1 μm to 1 mM) and the reduction of $Ru(NH_3)_6^{3+/2+}$ (10 μm to 10 mM) recorded at a potential sweep rate of 4 mVs$^{-1}$. Both redox species show well-defined sigmoidal voltammetric curves, characteristic of steady-state behavior at UMEs. Further, a near perfect scaling of the diffusion-controlled steady-state limiting current, $i_{ss}$, with mediator concentration ($r^2$ is 0.9999 for both mediators) was observed. Diffusion coefficients extracted from the slope of the plots, are 8.5×10$^{-6}$ cm$^2$ s$^{-1}$ for FcTMA$^+$ and 9.8×10$^{-6}$ cm$^2$ s$^{-1}$ for $Ru(NH_3)_6^{3+}$, in good agreement with literature values. In addition, both species show reversible behaviour, with a difference in quartile potentials (Tomeš criterion) of 59 mV for the entire concentration range.

Example 4

Sensing of Dopamine

Previous work on high density SWNT networks of <1% surface coverage, revealed a minimum sheet resistivity of 77 kΩ square$^{-1}$, at −10 V gate voltages where semiconducting SWNTs were turned on. The high network resistivity gave significant iR effects at similar 100 μm disk UMEs for detection of redox species of concentrations above 1 mM. However, surprisingly, the time response of the 1% network was very similar to that obtained at the 100% carbon nanotube network UMEs, described herein. The carbon nanotube network is a material that retains all the advantageous properties we have reported for the 1% SWNT network, such as low capacitance and very fast response times but has much lower resistivity, given the higher surface coverage. We set out to exploit further advantages of the carbon nanotube high surface coverage by investigating the electrochemical behavior of a dopamine. Dopamine is known to adsorb on carbon electrodes, making its concentration difficult to analyse using electrochemical techniques.

Dopamine can exhibit sluggish electron transfer kinetics at "classic" carbon electrodes unless rigorous steps are taken to eliminate surface contaminants and to increase exposed edge plane sites. Electron transfer rates may be accelerated through pretreatment processes but the reproducibility and stability of the enhanced electrochemical performance is variable and can be short lived (S. H. DuVall, R. L. McCreery, *Anal. Chem.* 1999, 71, 4594 and C. D. Allred, R. L. McCreery, *Anal. Chem.* 1992, 64, 444.). The carbon nanotube network possesses inherent characteristics (porosity, conductivity, crystallinity) essential for a reliable electroanalytical sensor for dopamine detection. Although it is known that oxygen functionalities on carbon nanotubes (created either through acid reflux or plasma ashing) can act as catalysts for dopamine electron transfer, here we use pristine, "as grown" carbon nanotube networks with no need for further processing.

FIG. 5a) shows CVs taken for the oxidation of dopamine in phosphate buffer saline (PBS) in the concentration range 1 $\mu$M to 1 mM, recorded at a potential sweep rate of 4 mV s$^{-1}$. The calculated quartile potentials are 80±1 mV indicating a departure from reversibility. The plot of limiting current vs. dopamine concentration in FIG. 5b), shows a near perfect scaling of $i_{ss}$ with concentration. Outstandingly, concentrations of 1 $\mu$M can be accurately detected. In order to assess the applicability of the carbon nanotube network UMEs for in-vivo measurements, we investigated the behaviour of dopamine under conditions that mimic in-vivo environment, i.e. 4% albumin in water (w/w).

FIG. 5c) shows CVs recorded for dopamine in albumin in the concentration range 10 $\mu$M to 1 mM, at a potential sweep rate of 4 mV s$^{-1}$ and FIG. 5d) shows the plot of limiting current against concentration. The decrease in limiting current when changing the background electrolyte from PBS to albumin is caused by the expected 20% decrease in the diffusion coefficient of albumin in the more viscous medium. The difference in quartile potentials increases to 180 mV, indicating more sluggish electron transfer kinetics. Surprisingly, in spite of no cleaning or pre-treatment procedures being performed, the carbon nanotube network UMEs exhibited very long lifetimes, and typically tens of measurements could be carried out with no decrease in the performance of the UME.

FIG. 5e) shows CVs for the oxidation of serotonin (with 0.1 M NaCl and 5 mM HEPES supporting electrolyte) recorded at 100 mV s$^{-1}$ on very high density SWNT electrodes. A drop of solution, ~10 $\mu$l, was placed on the surface of the SWNTs and covered a circular area of the electrode approximately 3 mm diameter. (i) and (ii) show CVs recorded for serotonin concentrations of 50 nM, 100 nM, 500 nM and 1 $\mu$M. The background response is also shown (black line). The peak current in the CV was found to scale linearly with serotonin concentration over the concentration range 50 nM-100 $\mu$M.

FIG. 6 shows: (a) AFM (5 $\mu$m×5 $\mu$m) and (b) FE-SEM images of Pt NPs deposited onto high density SWNT networks. The Pt NPs were deposited from a solution containing 2 mM K$_2$PtCl$_6$ in 0.5 M HClO$_4$ supporting electrolyte by cycling the electrode potential from 1.0 V to –0.40 V at a scan rate of 10 mV s$^{-1}$ (i) 1 cycle; (ii) 5 cycles and (iii) 10 cycles. The z full height scale of AFM images is 400 nm, whilst for the FE-SEM images it is 400 nm in (b i and ii) and 2 $\mu$m in (biii).

FIG. 7 shows a schematic (a) of one possible use of a SWNT network electrode as a transparent electrode. Here the electrode is on top of an inverted scanning laser confocal microscope. The electrode is poised at a potential where electrolysis of a redox couple present in solution causes the local fluorescence intensity to change. In this particular case Ru(bipy)$_3^{2+}$ which has relatively high fluorescence is oxidized at the electrode surface. This results in production of Ru(bipy)$_3^{3+}$ which is not fluorescently active at the excitation wavelength utilized (488 nm) and a resulting change in the local fluorescence profile. (b)-(d) show intensity time trace recorded at the surface of the SWNT network electrode (100 $\mu$m diameter), from the backside, as the electrode potential is swept positive to oxidize Ru(bipy)$_3^{2+}$, causing the local fluorescent intensity to decrease near to the surface of the electrode, as Ru(bipy)$_3^{2+}$ is depleted.

The invention claimed is:

1. An electrode for electrochemical analysis comprising:
   an insulating surface;
   a network of carbon nanotubes situated on the insulating surface;
   and
   an electrically conducting material in electrical contact with the carbon nanotubes;
   wherein network is of average thickness in the range of approximately 4 nm-approximately 200 nm.

2. An electrode according to claim 1 wherein the three-dimensional network covers more than 5% of the insulating surface.

3. An electrode according to claim 1 wherein each carbon nanotube is in contact with at least three other carbon nanotubes, and randomly oriented.

4. An electrode according to claim 1 wherein the carbon nanotubes are single-walled carbon nanotubes (SWNTs), or multi-walled carbon nanotubes (MWNTs).

5. An electrode according to claim 1 wherein the insulating surface is selected from silicon with a silicon oxide coating, quartz, an insulating surface coated with aluminium oxide, polymeric surfaces and combinations thereof.

6. An electrode according to claim 1 wherein the carbon nanotubes are pristine.

7. An electrode according to claim 1 wherein the electrochemical analysis is one or more of the analysis selected from the group consisting of bioelectrochemical systems, is in photochemical studies and spectro-chemical analysis.

8. An assay device or kit comprising an electrode according to claim 1.

9. An assay device or kit according to claim 8, further comprising a counter electrode and a reference electrode and preferably a flow cell and/or a recordal means.

10. A method of manufacturing an electrode comprising:
    depositing a quantity of catalytic nanoparticles onto an insulating surface;
    exposing the insulating surface to heat, a source of hydrogen gas, and a source of a carbon-containing gas to grow the nanotubes to a thickness of about 10 nm to about 200 nm in thickness above the insulating surface; and
    depositing an electrically conducting material on the insulating surface so that the electrically conducting material is in electrical contact with the carbon nanotubes.

11. A method of manufacturing according to claim 10 wherein the catalytic nanoparticles comprise cobalt, iron, nickel or other metals or combinations thereof, or insulating nanoparticles comprising diamond or silicon dioxide.

12. A method of manufacturing according to any of claims 10 and 11 wherein the carbon-containing gas is a C1-C$_5$ alcohol.

13. A method of electrochemically analysing a solution, comprising:
    providing an electrode with an insulating surface having a three-dimensional network of carbon nanotubes having a thickness of about 10 nm to about 200 nm situated thereon; wherein the carbon nanotubes are oriented substantially parallel to the insulating surface;

bringing a sample of the solution into contact with the carbon nanotubes; and applying a potential across the electrode to electrochemically analyse the sample.

14. A method of electrochemically analysing a solution according to claim 13 wherein the solution is a biological solution selected from natural or synthetic blood, plasma, urine, saliva, semen, amniotic fluid, bile, lymph, and combinations thereof; and/or wherein the solution contains a catecholamine.

15. An electrode for electrochemical analysis comprising:

an insulating surface;

a network of carbon nanotubes situated on the insulating surface;

and an electrically conducting material in electrical contact with the carbon nanotubes;

wherein the carbon nanotubes are oriented substantially parallel to the insulating surface, wherein the network comprises a thickness of at least four nanotubes and no thicker than 200 nm.

* * * * *